United States Patent [19]

Zupanick et al.

[11] Patent Number: 4,662,745
[45] Date of Patent: May 5, 1987

[54] REFLECTANCE AND LUMINESCENCE CALIBRATION PLATE HAVING A NEAR-LAMBERTIAN SURFACE AND METHOD FOR MAKING THE SAME

[75] Inventors: Joseph E. Zupanick, Richardson; Robert G. Maynard, Dallas, both of Tex.

[73] Assignee: Atlantic Richfield Company, Los Angeles, Calif.

[21] Appl. No.: 826,222

[22] Filed: Feb. 5, 1986

[51] Int. Cl.$^4$ ............................................... G01J 1/02
[52] U.S. Cl. ................................................... 356/243
[58] Field of Search ........................... 356/243; 51/319

[56] References Cited

U.S. PATENT DOCUMENTS 4,047,032 9/1977 Judge et al. ..................... 356/243 X
4,302,678 11/1981 Schiffert ........................... 250/461.1

FOREIGN PATENT DOCUMENTS 0072598 6/1979 Japan ..................................... 51/319
0090825 7/1980 Japan ..................................... 356/243

OTHER PUBLICATIONS

"Reflectivity Reference Standard for Toner Concentration Sensor", I.B.M. Technical Disclosure, Bilby, 11-1978.
"Requirements for Reflection Standards and Measurements of Their Reflection Values", Erb, Applied Optics, 2-1975, pp. 493–499.

Primary Examiner—Davis L. Willis
Assistant Examiner—S. A. Turner
Attorney, Agent, or Firm—Roderick W. MacDonald

[57] ABSTRACT

In order to provide an calibration plate having both known reflectance and known luminescence characteristics for calibrating and proving a radiometer, which calibration plate exhibits a near-Lambertian surface reflectance, a ceramic or glass coating containing a rare earth photoluminescent material is bonded to a surface of a rigid substrate, such as a steel plate, and the ceramic coating is thereafter sandblasted with a fine abrasive in good condition.

8 Claims, 2 Drawing Figures

REFLECTANCE AND LUMINESCENCE CALIBRATION PLATE HAVING A NEAR-LAMBERTIAN SURFACE AND METHOD FOR MAKING THE SAME

FIELD OF THE INVENTION

This invention relates to the testing and measurement arts and, more particularly, to calibration plates for determining the response of an instrument which is adapted to measure reflected light and luminescent light, in and near the visible range of the spectrum, emanating from a photoluminescent target. This invention further relates to methods for making such calibration plates.

BACKGROUND OF THE INVENTION

Optical instruments which measure target reflectance and luminescence are employed to indirectly determine diverse target characteristics. For example, one class of instrument measures the light energy emanating from a target batched in direct sunlight at wavelengths (a) within and (b) closely adjacent a selected Fraunhofer Line in the visible or near-visible portion of the spectrum. The results obtained include luminescence information and may be analyzed to classify target spectral characteristics from which mineralogical, geological, and other target characteristics can be deduced, often in conjunction with the analysis of additional target information obtained from measurements taken with other instruments.

In order to achieve the necessary measurement precision, instruments of the above mentioned class must be very closely calibrated, not only in the laboratory, but also in the field under rugged conditions. A typical initial laboratory calibration for an individual instrument requires the use of a standard target illuminated by a standard light source directed under standard conditions onto the standard target from which predetermined readings by the instrument under proof should be obtained. Any deviation from the expected readings may be used to recalibrate the instrument, to derive coefficients involved in the equations for reflectance and luminescence, and/or to develop correction factors to be applied to instrument readings taken in the field. Once a close laboratory calibration has been achieved, slight readjustment to (or slight revision of the correction factors used with) an individual instrument in the field can be performed if reliable field calibration targets are available.

It is possible to achieve effective field calibration of an instrument of this class using one or more calibration targets having known reflectance ratios, known near-Lambertian surface reflectance characteristics (i.e., the radiance being constant or nearly constant for any angle of reflection to the surface normal) and known zero luminescence characteristics. A suitable reflectance calibration target of this class is disclosed in copending U.S. patent application Ser. No. 651023, filed Sept. 17, 1984, entitled REFLECTANCE TEST PLATE HAVING A NEAR-LAMBERTIAN SURFACE AND METHOD FOR MAKING THE SAME, by Joseph E. Zupanick, and assigned to the same assignee as the present invention. However, those skilled in the art will appreciate that both the accuracy and the eae of field calibration would be substantially improved by the employment of field usable calibration plates having both known near-Lambertian reflectance characteristics and known luminescence characteristics which are other than zero in order to obtain a plurality of calibration points on an individual calibration curve.

OBJECTS OF THE INVENTION

It is therefore a broad object of our invention to provide an improved calibration target for field calibrating an instrument adapted to measure light energy emanating from a photoluminescent target within narrow frequency bands in the visible and near-visible region of the spectrum.

It is another broad object of our invention to provide a combined reflectance and luminescence standard for field calibrating an instrument of the above-mentioned class.

It is a more specific object of our invention to provide such a standard in the form of a calibration plate which is invariant with time and is sturdy and reliable for use in the laboratory and in the field and which may be readily and economically fabricated.

It is a further specific object of our invention to provide such a calibration plate which has a target surface exhibiting both a near-Lambertian reflectance characteristic and a determinable constant photoluminescent characteristic.

SUMMARY OF THE INVENTION

Briefly, these and other objects of the invention are achieved by bonding a brittle coating, which includes a photoluminescent material comprising a rare earth element, to a surface of a rigid substrate and sandblasting the coating with a fine abrasive which is in good condition.

DESCRIPTION OF THE DRAWING

The subject matter of the invention is particularly pointed out and distinctly claimed in the concluding portion of the specification. The invention, however, both as to organization and method of operation, may best be understood by reference to the following description taken in conjunction with the subjoined claims and the accompanying drawing of which:

DETAILED DESCRIPTION OF THE INVENTION

Figure 1:
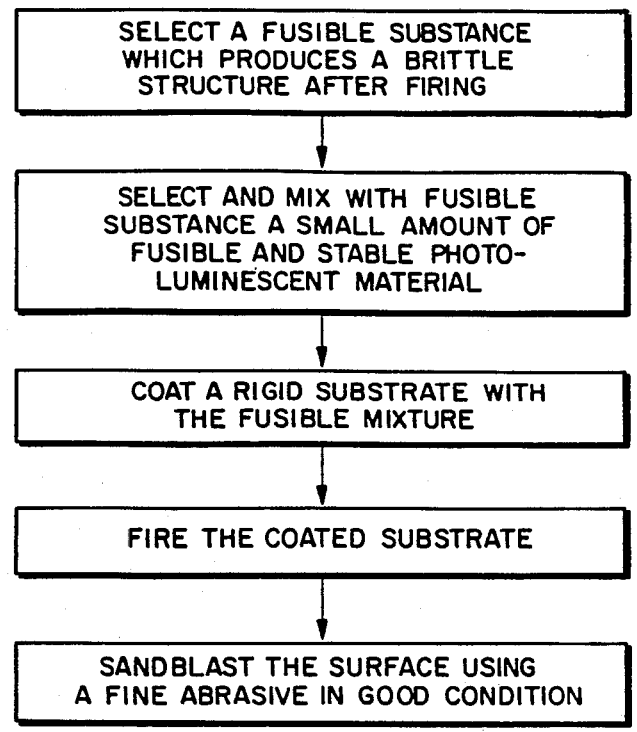
FIG. 1 is a flow diagram representing the basic steps for fabricating a calibration plate according to the present invention.

Referring first to FIG. 1, a generalized approach to the fabrication of a calibration plate according to the present invention is presented. A substance is first selected which can be transformed during a subsequent firing step into a brittle coating—which typically, comprises porcelain, enamel, ceramic and/or glass, the terms somewhat overlapping in the art and mixtures of ceramic and glass commonly used—on a rigid substrate having a planar surface. Preferably, a porcelain, enamel, ceramic and/or glass coating over the substrate is sought such that among the alternative (or combined) primary choices for the main ingredient(s) of the fusible material are china clay and finely powdered glass constituents. Care must be taken in the selection and use of any supplementary ingredients (which might be added, for example, to enhance bonding to the substrate) to insure that none are employed which are even slightly photoluminescent.

Next, a known photoluminescent ingredient is selected, and a quantity thereof is added to the fusible substance. The photoluminescent ingredient must meet several criteria: it must luminesce, when subjected to sunlight, in the visible or near visible region of the spectrum; it must be stable in the atmosphere; and it must be capable of being finely ground, mixed with the fusible substance and fired without changing its essential photoluminescent characteristic.

It has been determined that the rare earth elements in the Lanthanide Series (elements 57-71; i.e.: lanthanum, cerium, praseodymium, neodymium, promethium, samarium, europium, gadolinium, terbium, dysprosium, holmium, erbium, thulium, ytterbium, and lutecium), and particularly certain of their compounds, meet these criteria. More specifically, most sulfates, chlorides, fluorides, acetates, nitrates, carbonates, oxalates and oxides of these rare earth metals are suitable.

From among these, compounds of praseodymium have been found to be especially preferred. By way of example, praseodymium acetate is an excellent choice for mixing with a paste of mostly china clay to provide a mixture to be used to coat a steel plate which is subsequently fired to transform the coating into a photoluminescent ceramic layer on the outer plate surface. Similarly, praseodymium oxide has been found to be appropriate for mixing with a paste of mostly glass constituents to provide a mixture for application to a steel plate to produce, after firing, a photoluminescent glass layer on the outer plate surface. However, these examples should not be deemed limiting since, merely by way of example, successful calibration plate fabrication has been obtained using praseodymium acetate in a paste of mostly glass constituents.

The basic process for bonding ceramic, glass or like coatings to a rigid substrate, such as steel, are well known in the art. Briefly, as modified for employment during the fabrication of the subject calibration plates, the process generally involves overlaying all surfaces of the rigid substrate with a coating of a wetted mixture including prepared clay or glass constituent paste (or a combination) and the photoluminescent additive (and which may also include additional, non-photoluminescent additives to enhance the bonding processor or perform other routine functions in the firing step or to control the reflectance ratio of the end product). The coated plate is then subjected to high temperatures (typically in the range 1500 degrees F. to 2500 degrees F.) in a kiln or furnace at ambient pressure and environment for a sufficient length of time (on the order of five-ten minutes) to allow the coating material to fuse and adhere to the substrate. All surfaces of the substrate are preferably coated because the substrate and coating have different coefficients of expansion with temperature which could lead to a warped end product on cooldown if only a single surface were coated. The thickness of the brittle coating should be adequate to insure that the surface spectral characteristics are not altered when material is removed by the subsequent sandblasting step which should not completely penetrate the brittle coating. Thus, a useful variation of the process includes the application of a preliminary coating and a first firing followed by the application of a second coating (which includes the photoluminescent material) and a second firing.

Figure 2:
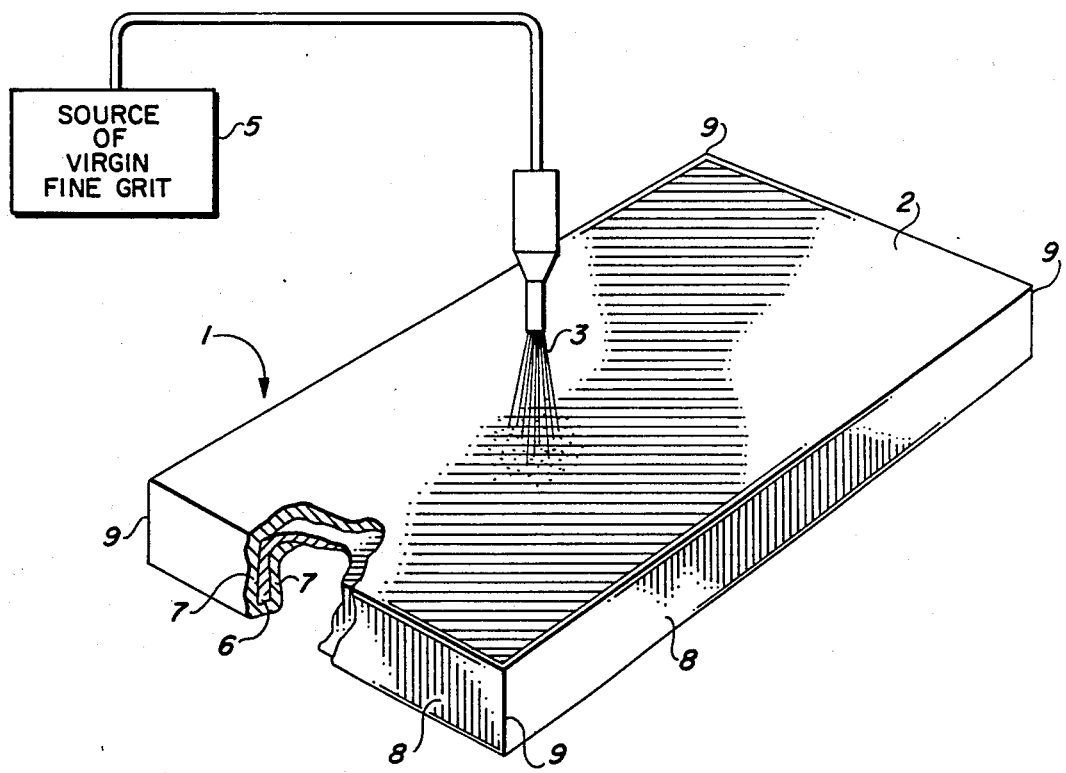
FIG. 2 is a pictorial view illustrating a sandblasting step employed in completing fabrication of the calibration plate which is shown partially cutaway.

As shown in the cutaway portion of the calibration plate 1 illustrated in FIG. 2, a steel substrate 6 is preferably overlaid on all surfaces with a ceramic and/or glass coating 7 of which the upper surface 2 receives a sandblasting treatment. In order to achieve rigidity in conjunction with relatively light weight, the edges 8 (and the corresponding edges out of view in FIG. 2) may be bent downwardly at a ninety degree angle and joined at the corners 9 to realize the desired rigid structure.

The calibration plate 1 is illustrated in FIG. 2 during the process of having its upper surface 2 prepared to take on a near-Lambertian reflectance characteristic which is imparted by the effect of abrasive 3 issuing from sandblaster nozzle 4 to impinge upon the upper surface 2. The abrasive 3 is supplied from a source 5 of fine grit. Preferably, the grit from the source 5 should be at least 60 fine, and particularly good results have been achieved with grit as fine as 240. (It is speculated that the particulate size might usefully be on the order of the wavelength of interest.)

It is especially important to note that the fine grit must be in good condition, each grain retaining its sharp edges, since a myriad randomly oriented angular (and not rounded) pits are sought. Thus, if common silica is the abrasive employed, it must not have previously been used; experience has shown that silica abrasive which has previously made only a single pass through the sandblaster will not produce the desired near-Lambertian surface. Tougher abrasive grit, such as silicon carbide, which is in good condition may be effective through more than a single use, but it is believed that the best results are nonetheless often obtained with virgin abrasive.

Consider the following example of the preparation of a calibration plate according to the present invention. A steel plate having down-turned edges for rigidity as noted above is prepared such that its planar upper surface is about 9½ inches square. All surfaces of the plate are coated with a paste comprising (as to the solid components):

ceramic frit (essentially fine china clay)—1000 parts
finely ground silicon dioxide—80 parts
finely ground hydrous sodium borate—19 parts
finely ground praseodymium acetate—1 part The silicon dioxide and hydrous sodium borate, in this example, are bulk vehicles for mixing with the praseodymium acetate to obtain a preliminarily uniform distribution of the praseodymium acetate when it is subsequently mixed with the ceramic frit. Additionally, the sodium borate acts as a flux which reduces eutectically the fusion temperature of the silicon dioxide and the praseodymium acetate. Thus, a preferred procedure is to first mix the preseodymium acetate with the hydrous sodium borate to obtain a first uniform mixture; next mix the first mixture with the silicon dioxide to obtain a second uniform mixture; and then uniformly blend the second mixture into the ceramic frit. Double distilled water is employed as the liquid in the mixtures.

The coated steel plate is fired in a kiln (in normal atmospheric environment) at a temperature of about 1500-1600 degrees F. for seven-ten minutes to drive off the water and fuse the photoluminescent layer to the substrate. Then, the plate is cooled very slowly (preferably over a period of at least twenty-four hours) to prevent the "doped" glass from shattering due to unrelieved thermal induced stress. Thereafter, the plate upper surface is sandblasted with fine grit in good condition to obtain the near-Lambertian reflectance characteristic.

A second example will serve to illustrate the preparation of a calibration plate in a variation of the process which involves two firing steps. All surfaces of a steel plate having down-turned edges as previously described are coated with a frit comprising very finely ground (200-325 mesh) borosilicate glass (an optical glass containing lead borosilicate) mixed with water. The coated plate is then placed on a conveyor belt which traverses on the order of fifty feet through a furnace at 1500–1600 degrees F. at a rate which obtains a firing time of seven-ten minutes.

After the plate has cooled, it is coated with a mixture of water, finely ground white pacifier and finely ground black oxide in proportion to obtain the desired reflectance rating and finely ground praseodymium oxide in a concentration on the order of about 1 part in 1000 to the black oxide. The plate is then passed through the furnace again at substantially the same rate, temperature and atmospherre to fire the second coat. After the second cooldown, the upper plate surface is sandblasted as previously described with fine grit in good condition to obtain the near-Lambertian reflectance characteristic. During the sandblasting step, care must be taken to avoid complete penetration of the second layer containing the rare earth additive.

A completed calibration plate must have its reflectance and luminescence characteristics measured under laboratory conditions before it can be used with confidence as a field standard. The reflectance ratio and diffusion of the sandblasted surface may be compared, under standard illumination conditions and at various angles, against a reference reflective surface. The reference reflective surface may be, for example, a Halon (trademark) disc previously calibrated by and obtainable from The Eastman-Kodak Company, a barium sulfate ($BaSO_4$) plate which has itself been calibrated with respect to a Halon disc, or any other reflectance standard exhibiting near-Lambertian surface reflectance and which can be certified back to the National Bureau of Standards.

The photoluminescent characteristics of a calibration plate may be determined using a procedure similar to that used to calibrate an instrument of the class previously discussed. The calibration plate is illuminated by a standard illuminant having know spectral distribution and frequency characteristics, and the total light energy issuing from the calibration plate within a narrow waveband of interest is measured and compared against corresponding measurements (or previously gathered data) taken of a similar calibration plate having known zero luminescence. The difference in the total light returned by the calibration plate under test is due to the photoluminescence component. Such measurements can be taken with a Farrand Photospectrometer or similar laboratory instrument, and the luminescence is typically measured at or near a useful Fraunhofer Line such as the sodium band situated at 5890 Angstroms.

While the principals of the invention have now been made clear in illustrative embodiments, there will be immediately obvious to those skilled in the art many modifications of structure, arrangements, proportions, elements, materials, and components, used in the practice of the invention which are particularly adapted for specific environments and operating requirements without departing from these principals.

We claim:

1. A method for making a calibration plate having a surface exhibiting a near-Lambertian reflectance characteristic and a determinable and constant photoluminescent characteristic comprising the steps of:
   (A) selecting a fusible substance which, after fusion and cooling, produces a brittle structure;
   (B) adding to the fusible substance, a photoluminescent ingredient comprising a rare earth element selected from the group including: lanthanum, cerium, praseodymium, neodymium, promethium, samarium, europium, gadolinium, terbium, dysprosium, holmium, erbium, thulium, ytterbium, and lutecium to provide a fusible mixture;
   (C) applying the fusible mixture as a coating to a surface of a rigid substrate;
   (D) firing the coated rigid substrate;
   (E) cooling the fired coated rigid substrate; and
   (F) sandblasting the outer surface of the fired coating employing a fine abrasive which is in good condition.

2. The method of claim 1 in which the photoluminescent material is a rare earth compound selected from the group including: sulfates, chlorides, fluorides, acetates, nitrates, carbonates, oxalates and oxides.

3. The method of claim 2 in which the rigid substrate comprises a steel plate, the fusible substance comprises china clay and the rare earth compound is praseodymium acetate.

4. The medoum of claim 2 in which the rigid substrate comprises a steel plate, the fusible substance comprises glass and the rare earth compound is praseodymium oxide.

5. A calibration plate having a surface exhibiting a near-Lambertian reflectance characteristic and a determinable and constant photoluminescent characteristic comprising:
   (A) a rigid substrate;
   (B) a brittle coating overlaying a surface of said substrate, said brittle coating including a photoluminescent material comprising a rare earth element selected from the group including: lanthanum, cerium, praseodymium, neodymium, promethium, samarium, europium, gadolinium, terbium, dysprosium, holmium, erbium, thulium, ytterbium, and lutecium; and
   (c) an outer surface of said brittle coating, which outer surface has been sandblasted using a fine abrasive in good condition.

6. The calibration plate of claim 5 in which said photoluminescent material is a rare each compound selected from the group including: sulfates, chlorides, fluorides, acetates, nitrates, carbonates, oxalates and oxides.

7. The calibration plate of claim 6 in which said rigid substrate comprises a steel plate, said brittle coating comprises ceramic and said rare earth compound is praseodymium acetate.

8. The calibration plate of claim 6 in which said rigid substrate comprises a steel plate, said brittle coating comprises glass and said rare earth compound is praseodymium oxide.

* * * * *